United States Patent [19]
Diehl et al.

[11] Patent Number: 5,147,884
[45] Date of Patent: Sep. 15, 1992

[54] PRESERVATIVE FOR AQUEOUS PRODUCTS AND SYSTEMS

[75] Inventors: Karl-Heinz Diehl, Norderstedt; Peter Oltmanns, Hamburg, both of Fed. Rep. of Germany

[73] Assignee: Sterling Drug Inc., New York, N.Y.

[21] Appl. No.: 479,126

[22] Filed: Feb. 12, 1990

[30] Foreign Application Priority Data

Feb. 11, 1989 [DE] Fed. Rep. of Germany ....... 3904099

[51] Int. Cl.$^5$ ..................... A01N 43/71; A01N 43/78; A01N 43/80; A01N 31/00
[52] U.S. Cl. ..................... 514/365; 514/367; 514/372; 514/396; 514/565; 514/706; 514/731; 514/738
[58] Field of Search ............... 514/738, 731, 714, 706, 514/360, 322, 367, 362, 565

[56] References Cited

U.S. PATENT DOCUMENTS 3,625,904  7/1968  Nosler et al. ................. 252/107
4,321,257  3/1982  Sipos ........................... 424/80

FOREIGN PATENT DOCUMENTS 0147222  7/1985  European Pat. Off. .
0147223  7/1985  European Pat. Off. .
1583994  12/1969  France .

OTHER PUBLICATIONS

P. Gilbert et al., Microbios, 19 125-141 (1977).

Primary Examiner—Leonard Schenkman
Assistant Examiner—T. J. Criares
Attorney, Agent, or Firm—John R. Everett

[57] ABSTRACT

An antimicrobial composition for preserving products or systems containing an aqueous phase comprising from 10 to 60% by weight or tert.-butyl hydroperoxide, from 3 to 50% by weight of a monophenylglycol ether of formulas I or II herein, and the remainder a diluent which is water, an organic solvent or a mixture of water and organic solvent; and a method of use of the antimicrobial composition. The antimicrobial composition may additionally include up to about 20% by weight of a biocide selected from certain non-halogenated phenols, certain heterocyclic compounds and guanidine, phthalimide and urea derivatives.

18 Claims, No Drawings

PRESERVATIVE FOR AQUEOUS PRODUCTS AND SYSTEMS

BACKGROUND OF THE INVENTION (a) 1. Field of the Invention

The invention relates to a preservative for systems or products containing an aqueous phase, for example dyes, paints, adhesives, aqueous emulsions such as drilling oil emulsions, cooling water circulation systems, for example in air-conditioning installations, and for other products requiring a preservative including those in the washing and cleaning products sector such as apparatus rinsing liquids.

(b) 2. Information Disclosure Statement

Products containing an aqueous phase can have a tendency, due to microbial activity, to discolor, form gas, change in consistency or form odors. This is especially so if the products comprise biologically degradable substances such as emulsifiers or protective colloids which make a suitable nutrient medium for bacteria.

Preservatives containing highly chlorinated phenols or organic mercury compounds or those based on formaldehyde are seldom used nowadays because of their poor environmental safety record and toxicity to humans. The general endeavour in developing novel preservatives lies in the direction of reducing the use of chemicals while retaining the same antimicrobial activity and therefore the discovery of new synergistic combinations of active substances based on known antimicrobial substances assumes considerable importance.

EP 147,222 and EP 147,223 disclose the use of tert.-butyl hydroperoxide (TBHP), whose biostatic properties are insufficient for its use alone as a preservative, in conjunction with compounds such as xylenol, cresol, phenylphenol and alkylated phenols, as well as aldehydes, heterocyclic or quaternary compounds for the preservation of motor fuels and refrigerant lubricants, or in conjunction with a fungicide as a wood preservative. However, such mixtures no longer meet current ecological requirements.

It is known from P. Gilbert et al., Microbios 19, 125–141 (1977) and U.S. Pat. No. 3,625,904 that certain phenylglycol ethers have antimicrobial properties. French Patent 1,583,994 discloses that certain phenylglycol ethers synergistically increase the activity of phenolic and quaternary ammonium disinfectant agents.

SUMMARY OF THE INVENTION

It is the object of the invention to provide a novel preservative for systems and products containing an aqueous phase based on a synergistic multi-component system which comprises low amounts of active substances and exhibits a broad spectrum of activity, even at low concentrations.

This objective is achieved by providing a preservative composition which comprises a 2-component system derived from tert.-butyl hydroperoxide (TBHP) and monophenylglycol ethers.

It has been found, surprisingly, that the combination of TBHP with a monophenylglycol ether possesses outstanding preservative activity for products or systems containing an aqueous phase. This is particularly surprising, since monophenylglycol ethers, for example 2-phenoxyethanol or phenoxypropanols which are known as solvents for a variety of uses, fail to manifest adequate antimicrobial activity even at acceptable concentration levels.

Thus, the invention provides an antimicrobial composition for preserving products and systems containing an aqueous phase comprising in admixture a) from about 10 to about 60% by weight of tert.-butyl hydroperoxide;

b) from about 3 to about 50% by weight of at least one monophenylglycol ether of the general formulas I and II:

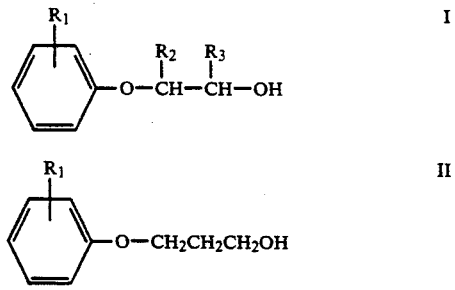

where $R_1$ is hydrogen or n-alkyl having from 1 to 3 carbon atoms, and $R_2$ and $R_3$ independently are hydrogen or methyl; and c) from 0 to about 85% by weight of a diluent.

DETAILED DESCRIPTION INCLUSIVE OF THE PREFERRED EMBODIMENTS

The antimicrobial composition of the invention contains two essential components and may contain, and preferably does contain, when formulated for end-use, a diluent for the two essential components. Thus, the composition can be formulated as a concentrate without a diluent, the diluent then being added prior to end-use, or may be formulated as a concentrate with a diluent ready for end-use.

One essential component is tert.-butyl hydroperoxide (TBHP), a well known and commercially available compound. The concentration of the TBHP will be in the range of from about 10 to about 60% by weight. When formulated or prepared for end-use, the antimicrobial composition preferably should for reason of handleability, contain no more than about 50% by weight of TBHP, more preferably from about 20 to about 30% by weight. Antimicrobial compositions of the invention containing 20 to 30% by weight of TBHP provide highly effective preservative activity when incorporated at concentrations of from about 0.1 to about 0.5% by weight into products and systems containing aqueous phases.

The second essential component is a monophenylglycol ether of the general formulas I or II hereinabove. As used herein, the term monophenylglycol ether includes mixtures of one or more of the ethers of formulas I and/or II. Such ethers belong to well known classes of compounds and are commercially available or can be prepared by known procedures. Examples of ethers which can be used are 2-phenoxyethanol, 2-(2-methylphenoxy)ethanol, 2-(3-methylphenoxyethanol), 2-(2-ethylphenoxy)ethanol, 2-(4-ethylphenoxy)ethanol, 3-phenoxy-1-propanol, 2-phenoxy-1-propanol, 1-phenoxy-2-propanol, 3-(2-methylphenoxy)-1-propanol, 3-(4-methylphenoxy)-1-propanol, 3-(2-ethylphenoxy)-1-propanol and 1-(4-ethylphenoxy)-2-propanol. Particularly preferred are the ethers of formulas I and II wherein $R_1$, $R_2$ and $R_3$ each is hydrogen, i.e., 2-phenoxyethanol and 3-phenoxy-1-propanol. The concentration of the monophenylglycol ether will be in the range of from about 3 to about 50% by weight, preferably 5 to 25% by weight.

Any mutually compatible ratio of TBHP to the monophenylglycol ether can be used. Generally the ratio of the TBHP to the monophenylglycol ether will be in the range of from about 10:1 to about 1:10, preferably about 3:1 to about 1:3.

As diluent for components 1 and 2 there may be employed water or an organic solvent or mixtures thereof, the main criteria for choosing a diluent being that components 1 and 2 as well as any additional ingredients, discussed hereinbelow, are either soluble or readily emulsifiable therein and compatible therewith, and that the diluent also is compatible with the aqueous product or system to be preserved. Suitable organic solvents are for example those belonging to the class of glycols such as, for example, alkylene glycol, e.g., ethylene glycol and 1,2-propylene glycol, dialkylene glycol, e.g., diethylene glycol, and trialkylene glycol, e.g., triethylene glycol, as well as corresponding mono- and dialkyl ethers thereof, where alkyl can be straight or branched and preferably has from 1 to 5 carbon atoms, e.g., the monomethyl, monoethyl, monopropyl and monobutyl ethers of ethylene glycol, 1,2-propylene glycol, diethylene glycol and triethylene glycol and the dimethyl, diethyl and dibutyl ethers of ethylene glycol, 1,2-propylene glycol, diethylene glycol and triethylene glycol.

The composition of the invention can be formulated as a solution or as an aqueous emulsion or dispersion. In the latter case, any anionic, cationic or nonionic surface active agent can be employed as emulsifier or dispersant which is compatible with the components of the composition. The selection of a particular surface active agent and the concentration thereof suitable for providing a stable emulsion or dispersion can be readily made by the skilled artisan.

It is a particularly surprising characteristic of the composition of the invention that a considerable increase in preservative activity results if there is additionally included therein an antimicrobially active substance known per se, viz., a known biocide, even algicidally and fungicidally active substances.

Any well known biocide is suitable for this purpose except one which is sensitive to oxidation, e.g., benzoisothiazolone which in the presence of a peroxide is oxidized to biocidally inactive saccharin. Preferably, the biocide is selected from the following groups:

1) phenols, except for the halogen derivatives thereof
2) heterocyclic compounds, for example, isothiazolinones, benzothiazoles, imidazoles, benzimidazoles and derivatives of these compounds
3) other algicidally or fungicidally active substances, for example, guanidine, phthalimide or urea derivatives.

The first group comprises especially phenols of the general formula:

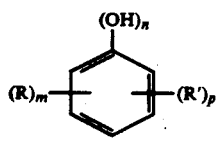

in which n is the integer 1,2 or 3, m and p each is the integer 0,1,2 or 3 and R and R' independently are lower-alkyl, lower-alkoxy, hydroxy-lower-alkyl, aryl, e.g., phenyl, aryl-lower-alkyl, e.g., benzyl or lower-alkylaryl, e.g., tolyl and xylyl. The terms lower-alkyl and lower-alkoxy refer to straight and branched alkyl and alkoxy. Preferably lower-alkyl and lower-alkoxy have from 1 to 4 carbon atoms. Preferred phenols are the xylenols and o-phenylphenol. Other suitable phenolic biocides are esters of p-hydroxybenzoic acid such as the lower-alkyl (as defined for the phenols above) esters, e.g., ethyl, methyl, butyl, isobutyl and propyl p-hydroxybenzoate.

The second group comprises, for example, the following biocidally active substances:
2-(thiocyanomethylthio)benzothiazole
2-(4-thiazolyl)-1H-benzimidazole
methyl 1-butylcarbamoyl-2-benzimidazolecarbamate
N-(n-propyl)-N-(2,4,6-trichlorophenoxyethyl)-N'-imidazolylurea
2-n-octy-4-isothiazolin-3-one
2-methyl-4-isothiazolin-3-one
5-chloro-2-methyl-4-isothiazolin-3-one
2-cyclohexyl-4-isothiazolin-3-one
2-dodecyl-4-isothiazolin-3-one
2-benzyl-4-isothiazolin-3-one Examples of biocidally active substances included in the third group are:
N-trichloromethylthiophthalimide
N-dichlorofluoromethylthio-N',N'-dimethyl-N-phenyl-sulfuric acid diamide
dodecylguanidine acetate
N-(n-propyl)-N-(2,4,6-trichlorophenoxyethyl)-N'-imidazolylurea
3-(3,4-dichlorophenyl)-1,1-dimethylurea The concentration of the biocide in the composition of the invention will usually not be less than 0.1% by weight and may be adjusted to suit the specific microbiological requirements. Thus, for example, if extremely powerful fungicidal activity is required, a fungicide such as, for example, 2-(thiocyanomethylthio)benzothiazole or 2-(4-thiazolyl)-1H-benzimidazole can be included at concentrations up to about 20% by weight to provide synergistically active preservative compositions. Where the solubility of a particular biocide is a problem, it is desirable to formulate the composition of the invention as an aqueous emulsion or dispersion with the aid of a suitable emulsifier or dispersant.

When a biocide additionally is employed in the composition of the invention, any mutually compatible ratio of TBHP to the biocide may be used. Depending on the specific use, this ratio of TBHP to the biocide may be 50:1 to 1:1, preferably 30:1 to 10:1. The ratio of TBHP to the biocide is essentially governed by their solubility in the chosen solvent or surfactant system and by the spectrum of antimicrobial activity required for the specific field of use.

In addition to the biocide, other additives such as are conventional in this art can be included in the composition of the invention.

The compositions of the invention can be readily prepared by dissolving the individual ingredients in a desired solvent or, where solubility is a problem, by emulsifying a mixture of the ingredients in a suitable diluent using conventional emulsification techniques.

The invention is illustrated by the following examples of specific embodiments but should not be limited thereto.

The TBHP employed in the examples was in the form of commercial 70 to 80% grades. The percentages by weight given in the examples denotes the concentrations of "active" ingredient.

To the right of each example, in a column entitled "Test Result", is given the number of inoculation cycles free of microbial growth reached with the composition described in that example in the preservative performance test described hereinbelow.

|  | % by wt. | Test Result |
|---|---|---|
| Example 1 | | |
| TBHP | 20 | |
| 3-Phenoxy-1-propanol | 20 | |
| Butyl diglycol | q.s. to 100 | 4 |
| Example 2 | | |
| TBHP | 25 | |
| 2-(Thiocyanomethylthio)-benzothiazole | 3 | |
| 3-Phenoxy-1-propanol | 15 | |
| Triethylene glycol | q.s. to 100 | 6 |
| Example 3 | | |
| TBHP | 18 | |
| 2-n-Octyl-4-isothiazolin-3-one | 3 | |
| 3-Phenoxy-1-propanol | 15 | |
| 1,2-Propylene glycol | q.s. to 100 | 5 |
| Example 4 | | |
| TBHP | 10 | |
| 2-(4-Thiazolyl)-1H-benzimidazole | 5 | |
| 3-Phenoxy-1-propanol | 20 | |
| Butyl diglycol | q.s. to 100 | 5 |
| Example 5 | | |
| TBHP | 30 | |
| 2-(Thiocyanomethylthio)-benzothiazole | 3 | |
| 3-Phenoxy-1-propanol | 10 | |
| Butyl diglycol | q.s. to 100 | 6 |
| Example 6 | | |
| TBHP | 30 | |
| 2-n-Octyl-4-isothiazolin-3-one | 5 | |
| 3-Phenoxy-1-propanol | 15 | |
| 1,2-Propylene glycol | q.s. to 100 | 7 |
| Example 7 | | |
| TBHP | 40 | |
| 2-n-Octyl-4-isothiazolin-3-one | 1 | |
| 3-Phenoxy-1-propanol | 5 | |
| 2-Propylene glycol | q.s. to 100 | 5 |
| Example 8 | | |
| TBHP | 10 | |
| 2-(4-Thiazolyl)-1H-benzimidazole | 3 | |
| 3-Phenoxy-1-propanol | 25 | |
| Triethylene glycol | q.s. to 100 | 6 |
| Example 9 | | |
| TBHP | 20 | |
| o-Phenylphenol | 5 | |
| 3-Phenoxy-1-propanol | 10 | |
| Sodium diphenyl oxide disulfonate | 10 | |
| Deionized water | q.s. to 100 | 5 |
| Example 10 | | |
| TBHP | 25 | |
| Butyl p-hydroxybenzoate | 5 | |
| 3-Phenoxy-1-propanol | 10 | |
| Sodium diphenyl oxide disulfonate | 10 | |
| Deionized water | q.s. to 100 | 6 |
| Example 11 | | |
| TBHP | 20 | |
| Dodecylguanidine acetate | 10 | |
| 3-Phenoxy-1-propanol | 10 | |

-continued

|  | % by wt. | Test Result |
|---|---|---|
| Sodium diphenyl oxide disulfonate | 10 | |
| Deionized water | q.s. to 100 | 7 |
| Example 12 | | |
| TBHP | 20 | |
| 5-Chloro-2-methyl-4-isothiazolin-3-one/2-methyl-4-isothiazolin-3-one in the ratio 3:1 | 3 | |
| 2-Phenoxyethanol | 20 | |
| Butyl diglycol | q.s. to 100 | 6 |
| Example 13 | | |
| TBHP | 25 | |
| 5-Chloro-2-methyl-4-isothiazolin-3-one/2-methyl-4-isothiazolin-3-one in the ratio 3:1 | 5 | |
| 2-Phenoxyethanol | 15 | |
| Sodium diphenyl oxide disulfonate | 5 | |
| Deionized water | q.s. to 100 | 6 |

The synergistic activity of the antimicrobial compositions of the invention was demonstrated by the results of a preservative performance test. A description of the test procedure used follows:

The formulation to be tested is incorporated at a concentration of 0.1% into a 50 g sample of a styrene acrylate dispersion paint (details of the paint composition are given hereinbelow). Two days after incorporation of the antimicrobial composition, the test mixture is first streaked onto casein peptone - soy meal peptone agar and inoculated with 0.2 ml of an inoculation solution consisting of a solution of a homogeneous suspension of the following microorganisms:
1) Escherichia coli
2) Pseudomonas aeruginosa
3) Micrococcus luteus
4) Klebsiella pneumoniae
5) Yeasts
6) Aspergillus niger The titer of the inoculation solution is not less than $10^8$ microorganisms/ml. The test mixture is then inoculated once a week and streaked once a week onto agar plates, the first streaking taking place immediately prior to the new inoculation. The assessment of the microbial growth of the streaks is carried out after three days' incubation at 22° C. Streaks which are free from growth are observed for a further two days and reassessed. The assessment of the antimicrobial potency of the antimicrobial composition is carried out on the basis of the microbial growth on the streaks. A test composition is the more potent, the longer is the period to the first appearance of microbial growth, i.e., the greater the number of inoculation cycles withstood.

The microbiological results of some of the tested antimicrobial compositions of the invention are given below. In each case there is stated the concentration of active substance in the dispersion paint test mixture and the number of growth-free inoculation cycles reached with the individual active substances (see Table 1) and with the active substances in combination (see Table 2).

In Tables 1 and 2, TBHP denotes tert.-butyl hydroperoxide, TCMTB denotes 2-(thiocyanomethylthio)-benzothiazole and thiabendazole denotes 2-(4-thiazolyl)-1H-benzimidazole.

TABLE 1

| Concentration (ppm) | TBHP | 3-Phenoxy-1-propanol | TCMTB | 2-n-Octyl-4-isothiazolin-3-one | Thiabendazole |
| --- | --- | --- | --- | --- | --- |
| | | Number of Innoculation Cycles | | | |
| 500 | 4 | 2 | 4 | 4 | 3 |
| 400 | 4 | 1 | 4 | 3 | 3 |
| 300 | 3 | 1 | 3 | 3 | 2 |
| 200 | 3 | — | 3 | 2 | 2 |
| 100 | 2 | — | 3 | 2 | 1 |
| 50 | 1 | — | 2 | 1 | |
| 30 | 1 | — | 2 | | |
| 10 | — | — | 1 | | |

TABLE 2

Concentration (ppm)

| TBHP | 200 | 200 | 200 | 200 | 200 | 200 | 200 | 200 | 200 | 300 | 300 | 300 | 300 | 300 | 300 | 300 | 300 | 300 |
| --- | --- | --- | --- | --- | --- | --- | --- | --- | --- | --- | --- | --- | --- | --- | --- | --- | --- | --- |
| 3-Phenoxy-1-propanol | 200 | 200 | 200 | 200 | 200 | 200 | 200 | 200 | 200 | 100 | 100 | 100 | 100 | 100 | 100 | 100 | 100 | 100 |
| TCMTB | 50 | 30 | 10 | | | | | | | 50 | 30 | 10 | | | | | | |
| 2-n-Octyl-4-iso-thiazolin-3-one | | | | 50 | 30 | 10 | | | | | | | 50 | 30 | 10 | | | |
| Thiabendazole | | | | | | | 50 | 30 | 10 | | | | | | | | | |
| Number of inoculation cycles | 7 | 6 | 5 | 6 | 5 | 5 | 6 | 5 | 5 | 7 | 6 | 5 | 6 | 6 | 5 | 6 | 5 | 5 |
| TBHP | 100 | 100 | 100 | 100 | 100 | 100 | 100 | 100 | 100 | 100 | 100 | 100 | 100 | 100 | 100 | 100 | 100 | 100 |
| 3-Phenoxy-1-propanol | 300 | 300 | 300 | 300 | 300 | 300 | 300 | 300 | 300 | 100 | 100 | 100 | 100 | 100 | 100 | | | |
| TCMTB | 50 | 30 | 10 | | | | | | | 50 | 30 | 10 | | | | | | |
| 2-n-Octyl-4-iso-thiazolin-3-one | | | | 50 | 30 | 10 | | | | | | | 50 | 30 | 10 | | | |
| Thiabendazole | | | | | | | 50 | 30 | 10 | | | | | | | 50 | 30 | 10 |
| Number of inoculation cycles | 6 | 6 | 5 | 6 | 5 | 4 | 6 | 5 | 5 | 6 | 5 | 4 | 5 | 4 | 4 | 5 | 4 | 4 |

The synergistic activity of the tested antimicrobial compositions of the invention is clearly evident from the above microbiological results.

For example, a combination of 200 ppm of TBHP with 200 ppm of 3-phenoxy-1-propanol and 50 ppm of 2-(thiocyanomethylthio)benzothiazole ensures freedom from growth in the test product over seven inoculation cycles. With the individual active substances, not more than three (TBHP or 3-phenoxy-1-propanol) inoculation cycles are reached at equal concentrations. Replacing the combination of the active substances (450 ppm) by one of the three individual active substances brings about freedom from growth of microorganisms over not more than four inoculation cycles. This clearly indicates the existence of a synergistic effect.

Comparable results were obtained with the remaining tested formulations.

A styrene acrylate indoor paint of the composition given below was prepared in the usual manner by stirring and homogenization:

| Components | % by wt. |
| --- | --- |
| Water | 24.352 |
| Sodium polyphosphate | 0.008 |
| Sodium hydroxide | 0.03 |
| Ammonium polyacrylate | 0.16 |
| Antifoaming agent | 0.30 |
| Calcium carbonate | 34.10 |
| Titanium dioxide | 4.90 |
| Chalk | 19.50 |
| Talc | 4.90 |
| White spirit (flash point about 37° C.) | 1.50 |
| High-boiling ester alcohol | 1.0 |
| Hydroxyethyl cellulose | 0.30 |
| Acrylic ester copolymer | 8.80 |
| Thixotropic agent based on polyurethane | 0.15 |

To the above paint composition there was added about 10 % by weight of water and 0.3 % by weight of the composition of Example 2, based on the total weight of the composition, and the resulting mixture was thoroughly homogenized. The resultant paint composition exhibited outstanding resistance to attack by the microorganisms identified hereinbefore.

We claim:

1. An antimicrobial composition for preserving products and systems containing an aqueous phase comprising in admixture
   a) from about 10 to about 60% by weight of tert.-butyl hydroperoxide;
   b) from about 3 to about 50% by weight of at least one monophenylglycol ether of the general formulas I and II:

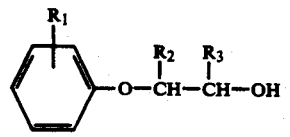

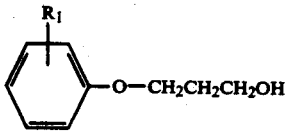

where $R_1$ is hydrogen or n-alkyl having from 1 to 3 carbon atoms, and $R_2$ and $R_3$ independently are hydrogen or methyl; and c) from 0 to about 85% by weight of a diluent.

2. The antimicrobial composition of claim 1 comprising from about 10 to about 40% by weight of tert.-butyl hydroperoxide; from about 5 to about 25% by weight of the monophenylglycol ether; and the remainder to 100% by weight of the diluent.

3. The antimicrobial composition of claim 2 comprising from about 20 to 30% by weight of tert.-butyl hydroperoxide; from about 5 to about 25% by weight of the monophenylglycol ether; and the remainder to 100% by weight of the diluent.

4. The antimicrobial composition of claims 1,2 or 3 wherein the diluent is water, an organic solvent or a mixture of water and the organic solvent 5. The antimicrobial composition of claim 4 wherein the organic solvent is selected from the group consisting of an alkylene glycol, a dialkylene glycol, a trialkylene glycol, an alkylene glycol monoalkyl ether, a dialkylene glycol monoalkyl ether, a triethylene glycol monoalkyl ether, an alkylene glycol dialkyl ether, a dialkylene glycol dialkyl ether and a trialkylene glycol dialkyl ether.

6. An antimicrobial composition according to claims 1,2 or 3 which additionally includes from about 0.1 to about 20% by weight of a biocide selected from the group consisting of a non-halogenated phenol, an isothiazolone, a benzothiazole, an imidazole, a benzimidazole, a quanidine derivative, a phthalimide derivative and a urea derivative.

7. The antimicrobial composition according to claim 6 which contains from about 2 to about 5% by weight of the biocide.

8. The antimicrobial composition of claim 6 wherein the biocide is a phenol of the general formula:

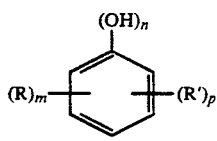

in which n is the integer 1,2 or 3, m and p each is the integer 0, 1,2 or 3, and R and R' independently are lower-alkyl, lower-alkoxy, hydroxy-lower-alkyl, aryl, aryl-lower-alkyl or lower-alkylaryl.

9. The antimicrobial composition of claim 8 wherein n is 1 and $(R)_m$ and $(R')_p$ each is methyl or n is 1, m is 0, and $(R')_p$ is o-phenyl.

10. The antimicrobial composition of claim 6 wherein the biocide is a lower-alkyl ester of p-hydroxybenzoic acid 11. An antimicrobial composition for preserving products and systems containing an aqueous phase which comprises from about 10 to about 40% by weight of tert.-butyl hydroperoxide; from about 5 to about 25% by weight of 2-phenoxyethanol or 3-phenoxy-1-propanol; from 0 to about 10% by weight of a biocide selected from the group consisting of o-phenylphenol, butyl p-hydroxybenzoate, 2-(thiocyanomethylthio)benzothiazole, 2-n-octyl-4-isothiazolin-3-one, 2-(4-thiazolyl)-1H-benzimidazole, 5-chloro-2-methyl-4-isothiazolin-3-one, 2-methyl4-isothiazolin-3-one and dodecylguanidine acetate; and from about 50 to about 65% by weight of a diluent selected from the group consisting of water, 1,2-propylene glycol, butyl diglycol and triethylene glycol, wherein said antimicrobial composition additionally comprises from about 5 to about 10% by weight of an anionic, nonionic or cationic surface active agent when the diluent is water.

12. The antimicrobial composition of claim 11 wherein the surface active agent is sodium diphenyl oxide disulfonate.

13. The antimicrobial composition of claim 11 which comprises 30% by weight of tert.-butyl hydroperoxide, 10% by weight of 3-phenoxy-1-propanol, 3% by weight of 2-(thiocyanomethylthio)benzothiazole and the remainder to 100% by weight butyl diglycol.

14. A method for preserving a product or system containing an aqueous phase which comprises incorporating in the product or system an antimicrobially effective amount of the composition according to claim 1.

15. The method of claim 14 wherein the amount of the antimicrobial composition incorporated is from about 0.1 to about 0.5% by weight.

16. A method for preserving a product or system containing an aqueous phase which comprises incorporating into the product or system an antimicrobially effective amount of the antimicrobial composition of claim 11.

17. The method of claim 16 wherein the surface active agent is sodium diphenyl oxide disulfonate.

18. The method of claim 16 wherein the amount of the antimicrobial composition incorporated is from about 0.1 to about 0.5% by weight.

* * * * *